US008929624B2

(12) United States Patent
Knoplioch et al.

(10) Patent No.: US 8,929,624 B2
(45) Date of Patent: Jan. 6, 2015

(54) SYSTEMS AND METHODS FOR COMPARING DIFFERENT MEDICAL IMAGES TO ANALYZE A STRUCTURE-OF-INTEREST

(75) Inventors: Jerome Francois Knoplioch, Buc (FR); Sylvie Jacquot-Ingles, Buc (FR); Cedric Hermel, Buc (FR); Sine Rosalina Woye, Buc (FR); Cathleen Cooper, Buc (FR)

(73) Assignee: General Electric Company, Schenectady, NY (US)

( * ) Notice: Subject to any disclaimer, the term of this patent is extended or adjusted under 35 U.S.C. 154(b) by 1071 days.

(21) Appl. No.: 12/954,739

(22) Filed: Nov. 26, 2010

(65) Prior Publication Data
US 2012/0134550 A1 May 31, 2012

(51) Int. Cl.
G06K 9/00 (2006.01)
A61B 19/00 (2006.01)

(52) U.S. Cl.
CPC ........... *A61B 19/56* (2013.01); *A61B 2019/461* (2013.01); *A61B 2019/5289* (2013.01)
USPC ............ 382/128; 382/173; 382/278; 345/419

(58) Field of Classification Search
CPC ............. A61B 19/56; A61B 2019/461; A61B 2019/5289; G06K 9/00
USPC ......... 382/128, 131, 173, 195, 199, 203, 276, 382/278, 282, 284, 286; 73/861, 761.02, 73/432.1; 378/4; 606/34; 345/156, 419, 345/581; 356/39; 128/922; 250/455
See application file for complete search history.

(56) References Cited

U.S. PATENT DOCUMENTS

| 7,616,799 | B2 | 11/2009 | Ramamurthy et al. |
| 7,747,050 | B2 | 6/2010 | Lau et al. |
| 7,936,922 | B2 * | 5/2011 | Berger ........................... 382/173 |
| 8,023,734 | B2 * | 9/2011 | Jolly et al. .................... 382/171 |
| 2001/0016684 | A1 * | 8/2001 | Shahidi .......................... 600/429 |
| 2005/0163358 | A1 * | 7/2005 | Moeller ......................... 382/128 |
| 2006/0025669 | A1 * | 2/2006 | Ramamurthy et al. ........ 600/407 |
| 2006/0147099 | A1 * | 7/2006 | Marshall et al. .............. 382/128 |
| 2007/0167697 | A1 | 7/2007 | Avila et al. |
| 2008/0008373 | A1 * | 1/2008 | Sirohey et al. ................ 382/131 |
| 2008/0118111 | A1 * | 5/2008 | Sirohey et al. ................ 382/106 |

(Continued)

FOREIGN PATENT DOCUMENTS

| WO | 0178607 A1 | 10/2001 |
| WO | 2005013841 A1 | 2/2005 |

OTHER PUBLICATIONS

Search Report and Written Opinion from corresponding PCT Application No. PCT/US2011/057054 dated Jan. 12, 2012.

*Primary Examiner* — Chan Park
*Assistant Examiner* — Mia M Thomas (57) ABSTRACT

A method of analyzing a structure-of-interest (SOI) in a patient. The method includes obtaining a first medical image of a patient. The first medical image includes an identified structure-of-interest (SOI). The identified SOI has a corresponding local measurement. The method also includes receiving a second medical image of the patient and selecting an SOI in the second medical image. The selected SOI has a corresponding local measurement. The method also includes automatically determining that the selected SOI is the identified SOI based on corresponding location data of the identified and selected SOIs, respectively, and linking the local measurements of the selected and identified SOI.

14 Claims, 8 Drawing Sheets

(56) References Cited

U.S. PATENT DOCUMENTS

| | | |
|---|---|---|
| 2008/0161687 A1 | 7/2008 | Suri et al. |
| 2009/0097732 A1* | 4/2009 | Bohm et al. ............ 382/132 |
| 2009/0116713 A1* | 5/2009 | Yan et al. ............. 382/128 |
| 2009/0175527 A1* | 7/2009 | Agliozzo et al. ........ 382/132 |
| 2009/0248441 A1 | 10/2009 | Okada |
| 2010/0128940 A1* | 5/2010 | Buelow et al. .......... 382/128 |
| 2011/0206250 A1* | 8/2011 | McGinnis et al. ....... 382/128 |

* cited by examiner

SYSTEMS AND METHODS FOR COMPARING DIFFERENT MEDICAL IMAGES TO ANALYZE A STRUCTURE-OF-INTEREST

BACKGROUND OF THE INVENTION

The subject matter herein relates generally to systems and methods for analyzing medical images, and more particularly, to systems and methods for monitoring a structure-of-interest (SOI) over time and/or monitoring the SOI's response to treatment.

One method of diagnosing patients for cancer includes comparing medical images acquired during different imaging sessions. For example, a patient may be scanned to obtain baseline CT imaging data of lesions within, for example, the patient's liver. A subsequent CT imaging session taken weeks or months later may help determine if the lesions have changed in size. Similarly, for patients that have already received a diagnosis that a suspected lesion is cancerous, the baseline CT imaging data may be taken prior to or at the beginning of treatment. After a predetermined amount of time and/or after a predetermined number of treatments, data from a subsequent CT imaging session may help determine if the treatment was effective.

However, when comparing the imaging data from different imaging sessions, a substantial amount of time may be used in loading, registering, and reviewing the images to determine if there has been a change in size of the lesions. For example, a radiologist may review a series of images from a first imaging session to locate and measure lesions from the first imaging session to establish baseline data. The measurements may then be loaded into a database or spreadsheet for subsequent analysis. When data from another imaging session is acquired, the radiologist may have to, again, review the series of newly acquired images, locate the lesions in the newly acquired images, and then measure the lesions to determine if a change in size has occurred. In a similar manner, imaging data from different imaging sessions may be compared to determine if a structure-of-interest has changed in function.

Accordingly, there is a need for systems and methods that reduce and/or simplify the process of analyzing imaging data to determine if an SOI has changed in size or function.

BRIEF DESCRIPTION OF THE INVENTION

In one embodiment, a method of analyzing a structure-of-interest (SOI) in a patient is provided. The method includes obtaining a first medical image of a patient. The first medical image includes an identified structure-of-interest (SOI). The identified SOI has a corresponding local measurement. The method also includes receiving a second medical image of the patient and selecting an SOI in the second medical image. The selected SOI has a corresponding local measurement. The method also includes automatically determining that the selected SOI is the identified SOI based on corresponding location data of the identified and selected SOIs, respectively, and linking the local measurements of the selected and identified SOI.

In another embodiment, a method for generating a report including local measurements of a structure-of-interest is provided. The method includes obtaining information relating to a first medical image of a patient that includes a structure-of-interest (SOI). The information includes a first local measurement of the SOI and first location data of the SOI. The first location data being indicative of where the SOI is located in the first medical image. The method also includes receiving a second medical image of the patient that includes the SOI and determining a second local measurement of the SOI and second location data of the SOI in the second medical image. The second location data is indicative of where the SOI is located in the second medical image. The method also includes automatically linking the second local measurement of the SOI with the first local measurement of the SOI based on the first location data and the second location data. The method further includes generating a report that includes the first and second local measurements.

In yet another embodiment, an image analysis system is provided that includes a database that is configured to store medical images. The database is configured to store a first medical image of a patient. The first medical image includes a structure-of-interest (SOI). The SOI has a first local measurement and first location data. The first location data is indicative of where the SOI is located in the first medical image. The system also includes a user interface that is configured to accept user inputs to select the SOI in a second medical image. The system also includes a processor that is configured to determine a second local measurement and second location data of the SOI in the second medical image. The second location data is indicative of where the SOI is located in the second medical image. The processor is also configured to automatically link the second local measurement to the first local measurement and generate a report that includes the first and second local measurements.

DETAILED DESCRIPTION OF THE INVENTION

Exemplary embodiments that are described in detail below provide systems and methods that facilitate analyzing structures-of-interests (SOIs), such as lesions, tumors, tissues, and the like in medical images. In particular embodiments, the systems and methods include analyzing measurements of an SOI from different medical images to diagnose the SOI, determine effectiveness of treating the SOI, and/or for clinical trial management. In some embodiments, the systems and methods may include analyzing measurements of an SOI from medical images acquired at different times (e.g., before and after treatment) or from medical images acquired at substantially the same time, but with different imaging modalities. Also, some embodiments may provide a user interface that is simpler and/or more user-friendly than known user interfaces.

It should be noted that although the various embodiments may be described in connection with one or more lesions in a liver, the methods and systems described herein are not limited to such particular uses. An SOI can be any anatomical structure in a patient in which it is desired to detect changes in the SOI. Such changes could be changes in size, including shape, and/or function, including level of function. By way of example only, the SOI may be changing in size due to disease or as a result of treatment or therapy. In other embodiments, the SOI is any anatomical structure within the patient that is desired to be observed. The SOI may be located within or on any anatomical organ or system. For example, the SOI may be located within or on a boundary of the lungs, liver, heart, brain, pancreas, skeletal muscular structures/system, and nerve structures/system, as well as other organs or identifiable systems or structures within a human or animal anatomy.

As used herein, an element or step recited in the singular and proceeded with the word "a" or "an" should be understood as not excluding plural of said elements or steps, unless such exclusion is explicitly stated. For example, a prior medical image may include first and second (or more) medical images. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. Furthermore, when an element is described as being based on a factor or parameter, the term "based on" should not be interpreted as the factor or parameter being the sole factor or parameter, but may include the possibility that the element is also based on another factor or parameter.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., modules, processors, or memories) may be implemented in a single piece of hardware (e.g., a general purpose signal processor or random access memory, hard disk, or the like) or multiple pieces of hardware. Similarly, programs may be stand alone programs, may be incorporated as subroutines in an operating system, may be functions in an installed software package, may be a software surface package that is run from a computer server remotely, and the like. It should be understood that the various embodiments are not limited to the arrangements and instrumentality shown in the drawings.

Figure 1:
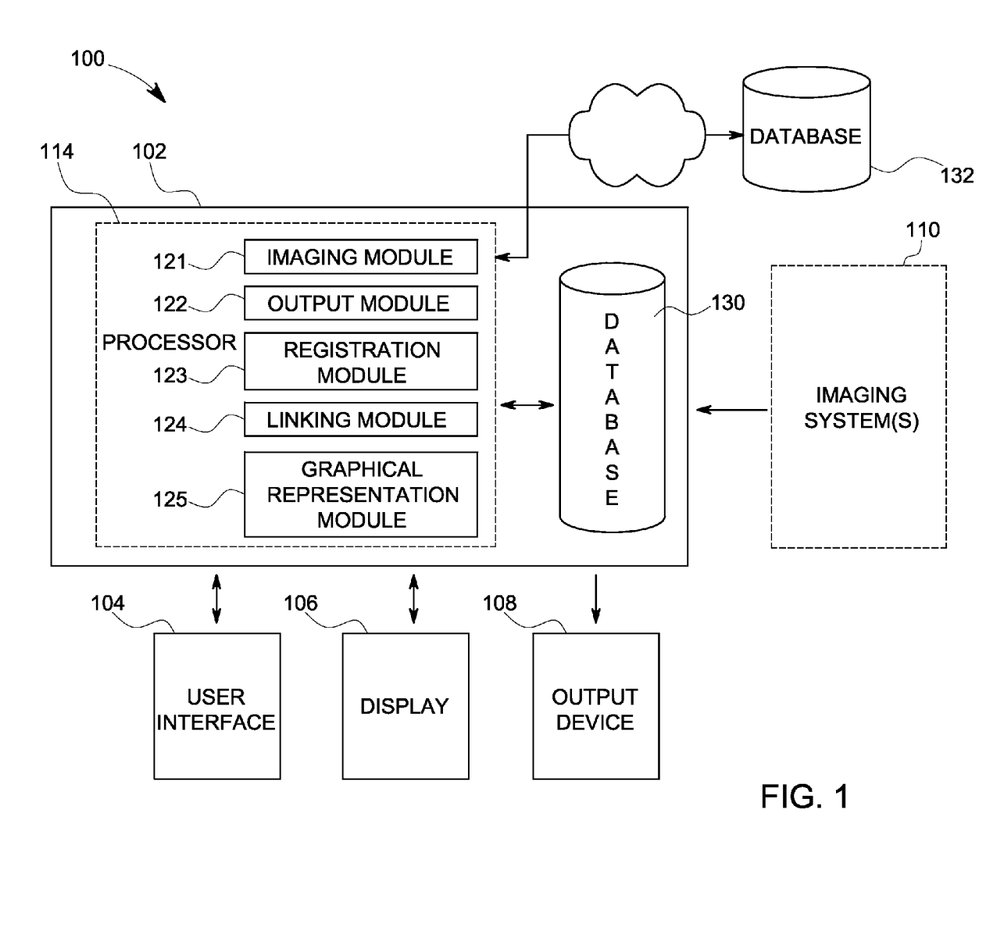
FIG. 1 is a block diagram of an exemplary system for analyzing medical imaging data in accordance with one embodiment.

FIG. 1 is a block diagram of an exemplary image analysis system 100 for analyzing medical imaging data. The system 100 includes a computing device or system 102 that is communicatively coupled to a user interface 104, a display 106, and an output device 108. The system 100 may be integrated into one component (e.g., a laptop computer) or may be several components that may or may not be located near each other. In alternative embodiments, the computing system 102 may be communicatively coupled to an imaging system(s) 110 that is/are configured to image a volume of interest (VOI) of a patient and communicate image data directly to the system 100. The imaging system 110 could include one or more modalities, such as, but not limited to, computed tomography (CT), positron emission tomography (PET), single photon emission computed tomography (SPECT), magnetic resonance (MR), and chest x-ray. In some embodiments, the imaging system 110 provides a stack or series of images taken along an examination axis. For example, a CT imaging system may acquire a series of images taken along an examination axis of a gantry and provide the series of images to the system 100 as imaging data or a dataset. The series of images may encompass the VOI, such as a torso and/or head of a patient.

As used herein, the phrase "different imaging sessions" may be imaging sessions acquired at different times (e.g., before and after treatment) and/or imaging sessions in which different imaging modalities were used. For example, a CT imaging session and a PET imaging session are different imaging sessions even though they may have occurred immediately after each other or were both acquired before treatment. First and second imaging sessions may also occur simultaneously or concurrently, such as with PET/CT imaging systems. Furthermore, multiple medical images may be reviewed in embodiments described herein. Similarly, the term "different medical images" may be images acquired at different times (e.g., during different imaging sessions) or by different imaging modalities. For example, embodiments may analyze a first medical image acquired before treatment, a second medical image acquired a month after treatment has begun, and a third medical image (or more) that was acquired after three months. First and second medical images may also be acquired during the same imaging session. For instance, the first medical image may be acquired when a tracer first enters the body and the second medical image may be acquired, during the same imaging session, after the tracer has been absorbed by an SOI.

Also, as used herein, the term "local measurement" includes any value or calculation that describes a characteristic of an SOI. The local measurement may relate to a size or morphology (e.g., length, width, diameter, volume, shape, contour, and the like) of the SOI or may also relate to a functional characteristic of the SOI. The term "size measurement" or "morphology measurement" may be any value or calculation that represents a dimension or shape of an SOI. For example, a size measurement (or morphology measurement) may be the longest diameter of a lesion, the shortest diameter of the lesion, or a ratio of different dimensions of the lesion (e.g., longest diameter/shortest diameter). The size measurement is not limited to distances, but may also represent other characteristics of the SOI, such as a density of the SOI or a volume of the SOI. Local measurements may be of a common type (e.g., both size measurements are of a longest diameter) or local measurements may be of a different type. The term "functional measurement" may be any value or calculation that represents a functional ability of the SOI. Examples of functional measurements include, but are not limited to, pixel statistics that are indicative of functional activity by the SOI, contrast or tracer uptake by the SOI, and shape or texture measurements that characterize properties of the SOI. In some circumstances, a measurement could be considered both a functional measurement and a size measurement.

The computing system 102 may include or be part of a server system, a workstation, a Picture Archiving and Communication System (PACS), a desktop computer, or a laptop computer. The above are only examples and the computing system 102 may be other types or kinds of systems. The computing system 102 includes a system controller 114, which may comprise a controller, processor, or other logic-based device. The system controller 114 may have or be communicatively coupled to modules for performing methods as described herein. The modules may include an imaging module 121, an output module 122, a registration module 123, a linking module 124, and a graphical representation module 125. Each of the modules 121-125 may be communicatively coupled to a memory or database 130 and/or communicatively coupled to a remote memory or database 132 via, for example, the internet or other communication network. Although the database 130 is shown as being shared by the modules 121-125, each module 121-125 may have a separate memory or database.

The imaging module 121 may be configured to receive imaging data from different imaging systems and communicate information about the imaging data to other modules. The output module 122 may receive and calculate data to provide the data in a more usable format for a user, computing device, or other module. For example, the output module 122 may generate a report, such as a summary table of local measurements, that is displayed to the user. The report may also be a dataset that is communicated to other modules and/or the databases 130 and/or 132. The registration module 123 may be configured to register or synchronize imaging datasets from different imaging sessions to facilitate identifying and analyzing SOIs. The linking module 124 may be configured to link two or more local measurements from different medical images. The graphical representation module 125 may be configured to generate images that communicate information to the user of the system. For example, the graphical representation module 125 may have a database of icons that represent different tools of the system 100 or notifications to the user.

In addition to the above, there may be several other modules or sub-modules of the system controller 114 that are not shown. For example, the system controller 114 may include modules that are used to analyze and interpret other data obtained by the system 100. Furthermore, the linking module 124 or the output module 122 may include sub-modules corresponding to various standards for analyzing data. There may be a sub-module that analyzes data according to various established standards, such as the Response Evaluation Criteria in Solid Tumors (RECIST, including 1.0 or 1.1) standard and standards established by the World Health Organization (WHO). Furthermore, modules (or sub-modules) may be added or modified as studies or standards are further developed.

The databases 130 and 132 may store data that can be retrieved by the components or modules of the system 100 and other remotely located systems through the internet or other communication network. The databases 130 and 132 may store data that the modules 121-125 may require in order to accomplish the functions of the modules 121-125. For example, the databases 130 and 132 may store imaging data from imaging sessions. The imaging data may be categorized or grouped in one or more manners, such as by patient, disease, gender, certain demographics, etc.

The user interface 104 is configured to accept or receive user inputs from a user of the system 100, such as a technician or radiologist. The user interface 104 may include at least one of a keyboard, a movable pointing device (e.g., mouse), a voice-activation system, and a touch-sensitive screen. The display 106 may also be the user interface 104. Furthermore, the output device 108 may be a printer, a removable storage device, the display 106 and/or the databases 130 and 132. Output generated by the system controller 114 may be formed into graphical representations that are displayed on the display 106 or stored into a storage device. For example, the output may include reports that compare local measurements of SOI's at different imaging sessions.

The modules 121-125 (and the system controller 114) may each include one or more processors, microprocessors, controllers, microcontrollers, or other logic based devices that operate based on instructions stored on a tangible and non-transitory computer readable storage medium. For example, the modules 121-125 may be embodied in one or more processors that operate based on hardwired instructions or software applications. The databases 130 and 132 may be or include electrically erasable programmable read only memory (EEPROM), simple read only memory (ROM), programmable read only memory (PROM), erasable programmable read only memory (EPROM), FLASH memory, a hard drive, or other type of computer memory.

Figure 2:
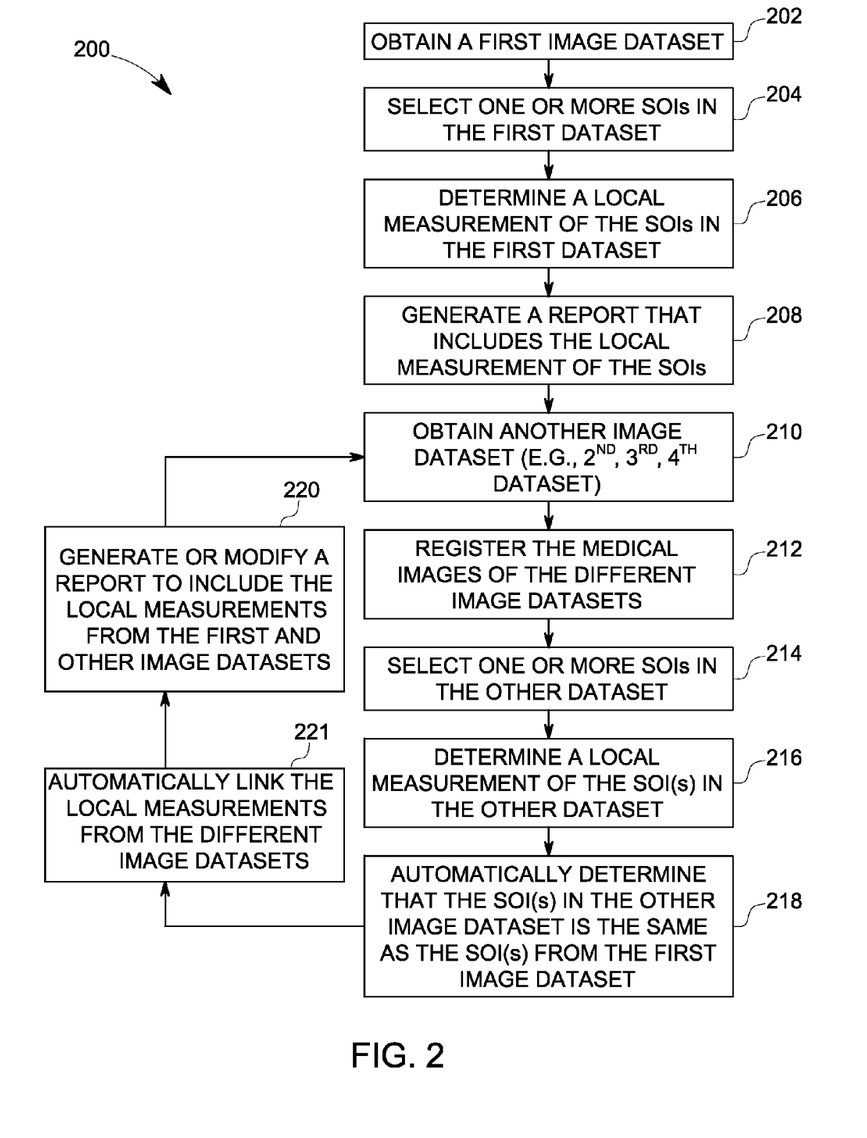
FIG. 2 is a block diagram illustrating a method of analyzing medical images in accordance with one embodiment.

FIG. 2 is a block diagram illustrating a method 200 of analyzing an SOI using different medical images. The method 200 includes obtaining at 202 a first image dataset of a patient. By way of example only, the first image dataset may be a baseline image dataset that provides a reference for future image datasets. The first image dataset may be acquired by retrieving the image dataset from a database or, alternatively, receiving the first image dataset from an imaging system. The first image dataset may include, for example, a series of medical images taken along an examination axis. In the exemplary embodiment, the series of medical images include a series of cross-sectional images (or slices) of a VOI of the patient. The cross-sectional images may have a predetermined thickness (e.g., 1.25 mm, 5 mm) in which each image includes a cross-section of one or more anatomical structures of the patient. As a specific example, the dataset may include a series of CT images of the patient's torso. The image dataset may also comprise three-dimensional (3D) medical images.

The method 200 also includes selecting or identifying at 204 one or more SOIs in the series of medical images. In some embodiments, the SOIs may be identified by a user of the system. For example, when reviewing each image in a series of images, the user may select the SOIs that the user would like to follow-up on in a subsequent review. The user may move a cursor key over a lesion and select the lesion. Alternatively, the user may use a touchscreen or tool to indicate the SOI.

In other embodiments, the selecting or identifying operation at 204 may be performed by a processor of the system 100. For example, after acquiring the image dataset, the user of the system may instruct the system 100 to identify potential SOIs in the image dataset. The system 100 may analyze the medical images to identify or select any image discontinuities in locations where the discontinuities should not exist. Optionally, the user may review the potential SOIs to confirm that the identified structures are SOIs. Accordingly, the step of selecting an SOI may be performed by an individual or the computing system.

After identifying the SOI(s), a local measurement may be determined at 206 for each identified SOI. In some embodiments, when selecting an SOI, the system 100 may automatically calculate a predetermined local measurement of the selected SOI. For instance, the output module 122 may analyze the contours of the lesion in the respective medical image and calculate a longest diameter and/or other local measurements (e.g., short axis). The Volume Viewer application from the Advantage Workstation by GE Healthcare has such a feature that automatically analyzes the contour of a structure-of-interest. The standards established by RECIST 1.1 and WHO identify exemplary size measurements that may be measured in various embodiments. The local measurement may be stored in the databases 130 and/or 132 along with other information (e.g., type of imaging modality, patient identification, the order number of the medical image in the series). In some embodiments, the user may be prompted to identify the type or kind of local measurement. For example, a query may appear on the display or user interface that asks the user to identify the local measurement as, for example, the longest diameter or shortest axis. In some embodiments, the user may determine the desired size measurement by, for example, drawing a line from one boundary of the SOI through the SOI to another boundary. A length of the line may then be calculated by the system 100 to determine the local measurement.

The method 200 may include generating at 208 a report that includes the local measurement(s) and other information about the SOIs. For example, the report may include the local measurements for each identified SOI in addition to the date of imaging, type of imaging modality, and axial location of the medical image. The report may be saved and stored within at least one of the databases 130 and 132. In some embodiments, the report may include or be linked to the medical image(s) from which the SOIs were identified and measured. As such, when the report is subsequently retrieved by a user, the user may review the local measurements and other information and also view the medical images from which the local measurements were obtained.

The method 200 may also include obtaining at 210 a second image dataset that has, for example, a series of medical images. By way of example, the second image dataset may be medical images acquired from a later imaging session. The second image dataset may be acquired by retrieving the image dataset from a database or, alternatively, receiving the second image dataset from an imaging system. At 212, the first and second image datasets may be registered or synchronized with each other. For example, when the first and second image datasets are registered, each of the medical images of the first and second series is associated with a corresponding medical image of the other series. For instance, each medical image from the first series will be associated with a corresponding one medical image from the second series that has the same (or nearly the same) axial location within the VOI. Furthermore, registration of the medical images may also account for in-plane rotation and/or translation. For example, during a second imaging session, the patient may be more tilted in one rotational direction or more shifted in one lateral direction as compared to the patient's position during the first imaging session. Registration of the medical images may account for these differences. Furthermore, in addition to two-dimensional images, embodiments described herein may be capable of registering three-dimensional images.

Registration may be performed by the registration module 123. For example, the registration module 123 may compare the medical images in each of the first and second image datasets to correlate and/or adjust the medical images. Alternatively, the registering operation 212 may be performed by a user of the system. The user may scroll through the medical images and select corresponding points that should be associated or linked with each other.

Before or after registering the first and second image datasets, SOIs in the second image dataset may be selected at 214 and local measurements of the SOIs may be determined at 216. The selecting and determining operations 214 and 216 may be performed in a similar manner as described above with respect to the selecting and determining operations 204 and 206 of the first image dataset.

Embodiments described herein may automatically link local measurements of an SOI from one image dataset to other local measurements of the same SOI from other image datasets. For example, the method 200 may include automatically determining at 218 that a selected SOI in a second medical image is the same SOI from a first medical image. The automatic determination may be based on the corresponding locations of the SOIs in their respective medical images. More specifically, location data that is indicative of where the SOIs are located in the first and second medical images may be used to determine if the selected SOI in the second medical image is the same SOI found in the first medical image. For example, the location data may comprise coordinates of the various points that define the SOI in the medical image and/or that define a line used to determine a size measurement. The location data may also comprise various points that define an area selected by a user. For example, the user may draw a line, oval, or square where the SOI is located in the medical image. Linking rules may then be applied to the location data to determine if the SOIs are the same SOI and/or to determine if the new local measurement should be linked with a previous local measurement. In addition or in the alternative, the location data may comprise vectors that define a location on the corresponding medical image.

Various algorithms may be used in determining whether SOIs from different medical images are the same SOI and/or in determining whether two local measurements should be linked together. For example, after the SOI in a medical image is identified, the system 100 may determine location data of the SOI. In some embodiments, the location data may include, for example, locations of points in a coordinate system that define at least one of a line that represents a size measurement (e.g., longest axis) or a perimeter or boundary of the SOI in the medical image.

Generally, the computing system may determine a separation distance between the SOIs based on the respective location data. For example, the location data may include the location of a center or centroid of the SOI. The center may be calculated using known centroid analysis programs. The center may be assigned coordinates or a vector that locates the center with respect to a predetermined reference point in the medical image. For example, x-y coordinates may identify where the center of the SOI is located with respect to a corner of the medical image or with respect to a landmark in the image (e.g., spine). In such embodiments, the separation distance may be defined as a distance that extends between the centers of the SOI in the first and second medical images may be calculated. A linking rule may then be applied to determine whether the separation distance is less than a predetermined value (e.g., 10 mm). If the separation distance is less than the predetermined value, the SOIs of the first and second medical images may be characterized as being the same SOI. Likewise, the corresponding size measurements of the SOIs may then be automatically linked together to describe the same SOI at different points in time.

Various other linking rules may be used to determine a separation distance or distances between the SOIs. For instance, two linear measurements (e.g., two lines of points) of the SOI in different medical images may be analyzed to determine if the local measurements should be linked together. By way of one example, if the shortest distance between points of the two lines (i.e., a first separation distance) is less than a predetermined value and if each of these points is within a set distance from a middle point of the corresponding line (i.e., a second separation distance), then the two measurements describe the same SOI and the two measurements may be automatically linked. As another example, if a shortest distance between a representative point of one linear measurement (e.g., a center of a line) and any point from the other linear measurement is less than a predetermined distance, then the two linear measurements may describe the same SOI.

Furthermore, an SOI may be defined by 2D or 3D regions (e.g., closed polygons, pixel or voxel definition). A 2D or 3D region may be linked to a linear measurement if more than a predetermined fraction of the line that represents the linear measurement is within the region (i.e., if a certain fraction of the line exists within the region). The certain fraction may be, for example, more than half a length of the line or any portion of the line that is within the region.

In addition to the above, local measurements from one 2D or 3D region may be linked to local measurements of another 2D or 3D region if the intersection (or overlap) of the different regions is more than a predetermined fraction of the smaller of the two regions. For example, in some embodiments, the location data may include an area determined by boundary points. The highest and lowest points of the SOI along a vertical axis of the image may be identified and the highest and lowest points along a horizontal axis of the image may be identified. These points may be used to define a rectangle that encloses the SOI. The linking module 124 may query whether the rectangles from the SOIs of the different medical images at least partially overlap each other or overlap each other by a predetermined fraction. If the rectangles from the SOIs of the different medical images satisfy the linking rule, the SOIs may be characterized as being the same SOI and the corresponding local measurements of the SOIs may then be linked together in a report.

The method 200 also includes automatically linking at 221 the local measurements from the different datasets. In particular embodiments, after satisfying one or more of the linking rules, such as those described above, the local measurements associated with the SOIs may be linked together. For example, after a new local measurement is determined and/or after the new SOI is selected, the computing system automatically (i.e., without receiving a separate user command to proceed) determines whether the new local measurement and/or the new SOI should be linked together. If the linking rule(s) is satisfied, the new local measurement is automatically displayed to the user in a manner that facilitates comparison between the new local measurement and any other known local measurements for the corresponding SOI. For instance, the local measurements may be displayed in a common graphic, such as the report 300 shown in FIG. 6 below. The local measurements may be displayed side-by-side.

In more particular embodiments, the computing system automatically calculates a mathematical relationship between the local measurements that facilitates comparison. For each SOI, the linked local measurements of the same type may be compared to a baseline local measurement of the same type. For example, the longest diameter calculated at separate time points T1, T2, and T3 may be shown for comparison, and the short axis calculated at separate time points T1, T2, and T3 may also be shown for comparison. An increase or decrease with respect to the baseline local measurement (e.g., percentage or change in value) may be shown along with the local measurements. In some embodiments, the graphical representation that represents the report is saved/stored in one or more of the databases thereby allowing a quicker retrieval.

In some embodiments, different local measurements of the same SOI may be grouped together. In some cases, the different local measurements of the same SOI may be determined from different medical images that were acquired at substantially the same time, but by different modalities. For example, a first local measurement (e.g., longest diameter) of an SOI may be determined in the first medical image (e.g., CT image). A second local measurement (e.g., level of functional activity) may be determined from a second medical image (PET image). If one or more linking rules are satisfied, the first and second local measurements may be linked and automatically displayed together. The two local measurements may be grouped together and shown to the user. For example, the two local measurements may be shown in a single cell of the report, such as the report 300 shown in FIG. 6. Accordingly, the user may be able to simultaneously view size information and functional information about the SOI.

Furthermore, in some cases, the multiple local measurements of the same SOI may be from the same medical image. By way of one example, the longest diameter, shortest axis, ratio of the diameter and axis, and, volume may all be grouped together and simultaneously shown. The various local measurements may be grouped together in a single cell of the report similar to the report 300 shown in FIG. 6.

In some embodiments, when local measurements are linked together, the computing system may automatically save/store the local measurements in such a manner that when a user would like to review the local measurements of SOI at a later date, a single command from the user may cause all of the linked local measurements to be retrieved. For instance, a user may not have to separately retrieve the local measurements. Furthermore, in some cases when local measurements are linked, the computing system may automatically determine a mathematical relationship between the local measurements and store/save the mathematical relationship with the local measurements. Such automatic linkage may reduce time and simplify workflow.

The method 200 may also include generating at 220 a report that includes the local measurements from the different medical images. The local measurements may be used to determine whether an SOI has changed in size over a period of time or has changed in some other manner (e.g., function). With respect to functional change, a level of tracer or contrast uptake may indicate change in activity of a tumor. As discussed above, the local measurements may also be derived from medical images that occurred at substantially the same time (e.g., before treatment) with different imaging modalities. The generating operation 220 may include generating a new report with the previously obtained local measurements and the newly obtained local measurements. The generating operation 220 may also include updating or modifying a previous report to include the newly obtained local measurements. The report may be represented by graphical images that are displayed to the user, or the report may be a dataset that is stored in the databases 130 and/or 132. The generating operation 220 may occur automatically (e.g., without additional commands from the user) after it is determined that two or more SOIs satisfy at least one linking rule.

As shown in FIG. 2, the steps 210, 212, 214, 216, 218, 221, and 220 may then be repeated with other image datasets.

Figure 3:
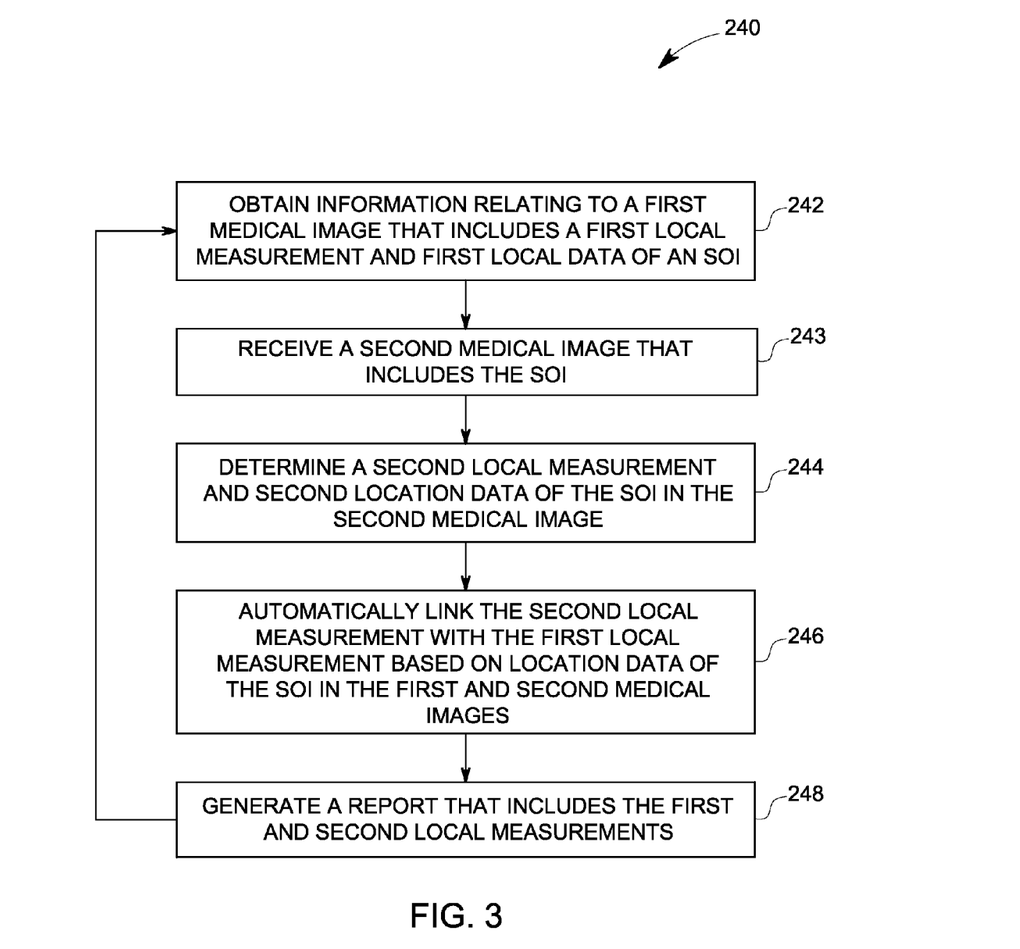
FIG. 3 is a block diagram illustrating a method of automatically linking local measurements of a structure of interest (SOI).

FIG. 3 is a block diagram illustrating a method 240 of automatically linking local measurements of an SOI. The method 240 may also be used in other methods, such as methods for analyzing an SOI in different medical images, methods for diagnosing an SOI, or methods for generating a report. The method 240 includes obtaining at 242 information relating to a first (e.g., prior) medical image of a patient that includes an SOI. The obtaining operation at 242 may include, for example, retrieving the first medical image from a dataset stored in a database and/or also acquiring the dataset using an imaging system. The first medical image may be one or more medical images from a series of medical images in a dataset. The information may include a first local measurement of the SOI and first location data of the SOI. The first location data may be indicative of where the SOI is located in the first medical image. The first location data may include a set of points in a coordinate system. For example, the first location data may be similar to the location data as described above with reference to the method 200.

The method 240 also includes receiving at 243 a second (e.g., later) medical image of the patient that includes the SOI. The receiving operation 243 includes, for example, retrieving the second medical image from a dataset stored in a database and also acquiring the dataset from an imaging system. The second medical image may be one or medical images from a series of medical images in a dataset. The second medical image may be acquired through an imaging modality that is the same imaging modality used to acquire the first medical image. Alternatively, the first and second medical images may be acquired by different imaging modalities. The method 240 also includes determining at 244 a second local measurement of the SOI and second location data of the SOI in the second medical image. The second local measurement may be determined as described above. The second location data may be indicative of where the SOI is located in the second medical image. For example, the second location data may be similar to the location data as described above with reference to the method 200.

In addition, the method 240 includes automatically linking at 246 the second local measurement of the SOI with the first local measurement of the SOI based on the first location data and the second location data. For example, the linking module 124 may apply one or more of the linking rules described above to determine whether the SOI in the second and first medical images is, in fact, the same SOI and to also link the local measurements. The method 240 may also include generating at 248 a report that includes the first and second local measurements. As described above, "generating a report" may include creating a new report or modifying a first report to include the second local measurements. The report may be displayed to a user or may be stored as a dataset. The steps of 242, 243, 244, 246, and 248 may then be repeated when second medical images are obtained. The information obtained in step 242 may include the report that was previously generated and the medical images used to generate the report.

Figure 4:
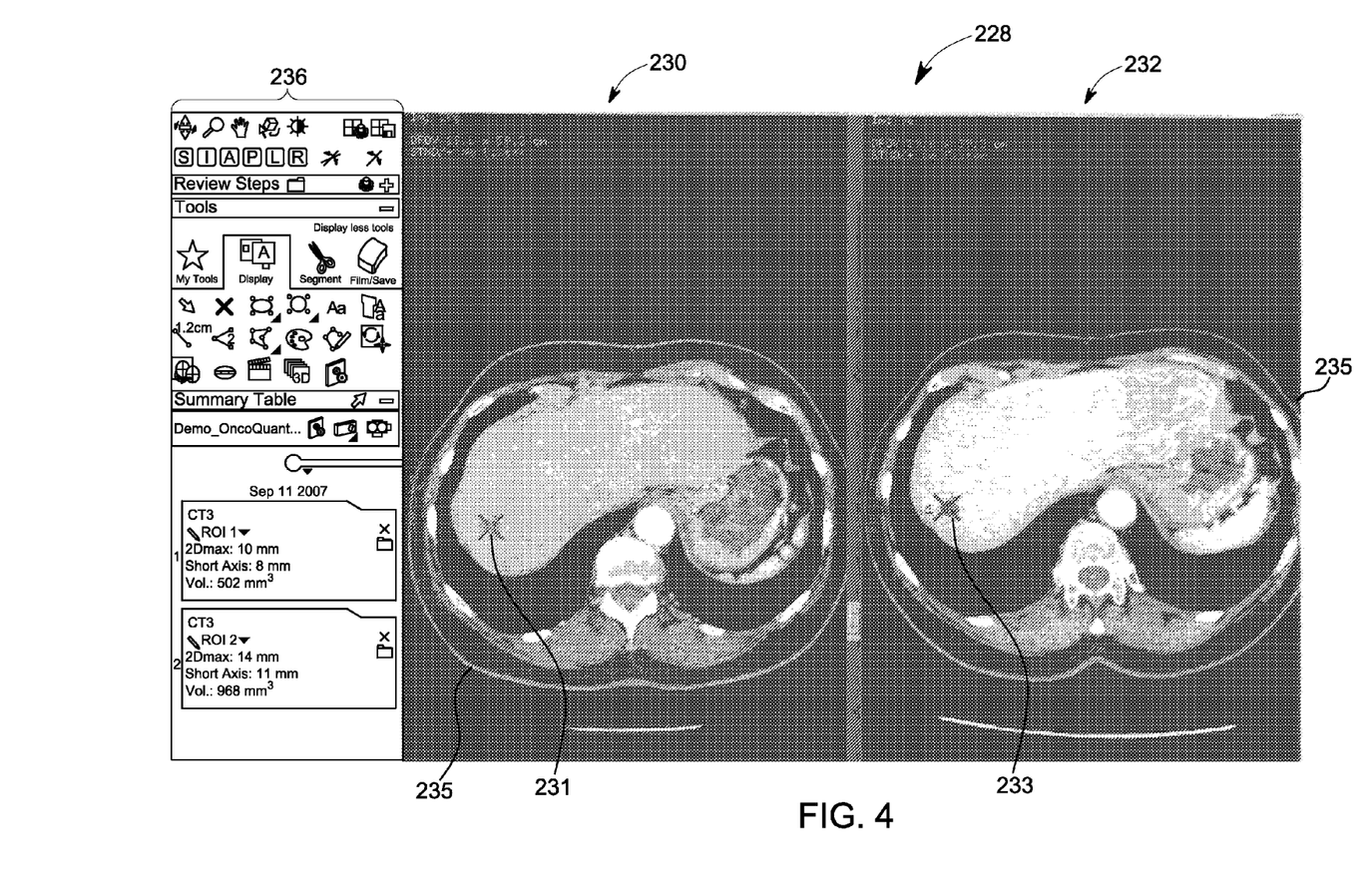
FIG. 4 illustrates a user display in accordance with one embodiment that shows different medical images.

FIG. 4 illustrates a user display 228 in accordance with one embodiment that shows different first and second medical images 230 and 232 acquired at different imaging sessions. In the illustrated embodiment, the first medical image 230 was acquired at a first or baseline time period and the second medical image 232 was acquired at a second later time period. The first and second medical images 230 and 232 are cross-sectional images of a patient 235. In the illustrated embodiment, the cross-sections were obtained at substantially the same axial position and, as such, the first and second medical images 230 and 232 may be registered with each other. The first and second medical images 230 and 232 show various anatomical structures of the patient 235 including a first SOI 231 in the first medical image 230 and a second SOI 233 in the second medical image 232. Since the first and second medical images 230 and 232 are registered, the user may suspect that the SOIs 231 and 233 are the same SOI. The linking module may apply one or more of the linking rules described above to determine if the SOIs 231 and 233 are the same SOI at different points in time.

For example, the user may draw a line across the SOI 233 to determine a local measurement (e.g., longest diameter). After drawing the line, the computing system may automatically apply a linking rule. If the linking rule is satisfied, the local measurement may then be automatically linked to a local measurement that was previously obtained. The automatic linkage may be similar to that described above. For instance, a report may be automatically displayed to the user that shows the local measurements together. Also shown in FIG. 4, the user display 228 may include a pane 236 that has several icons that initiate different tools for analyzing the first and second medical images 230 and 232.

Figure 5:
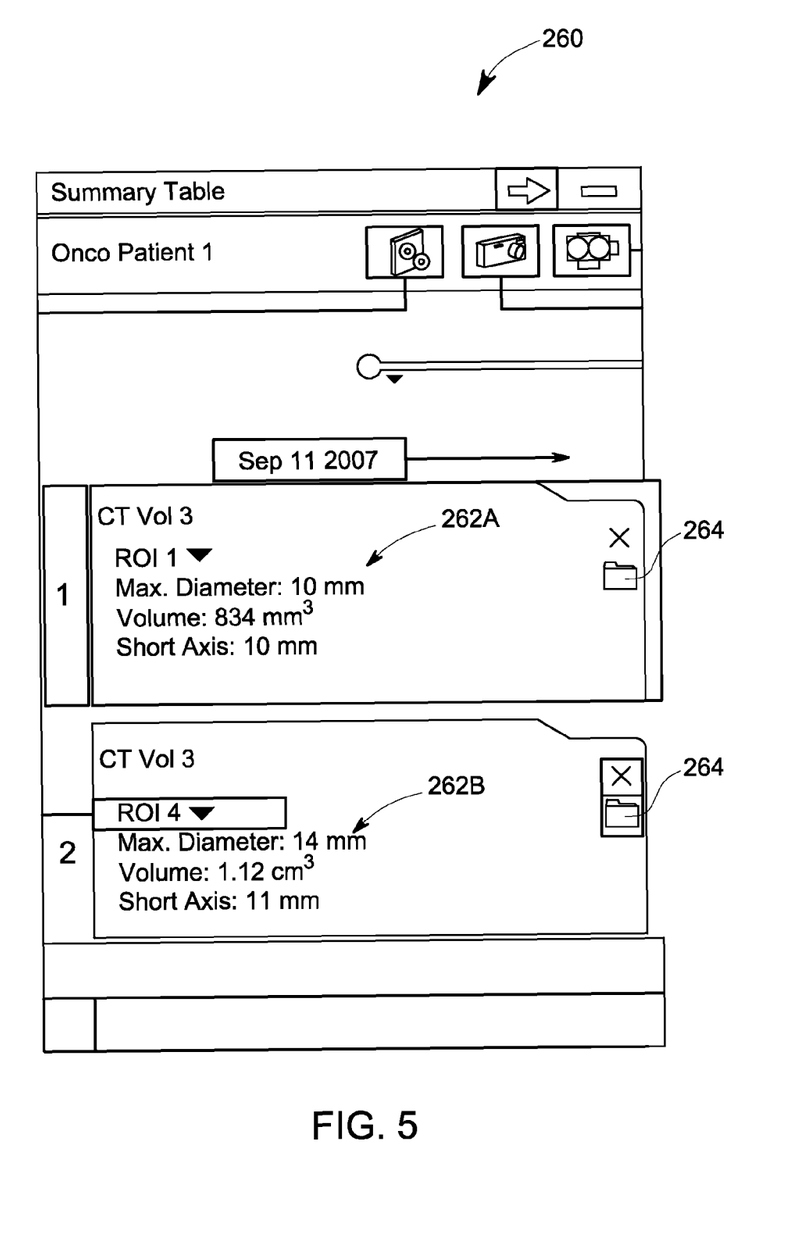
FIG. 5 illustrates a report that may be displayed to the user of the system of FIG. 1.

FIG. 5 illustrates a report 260 that may be displayed to the user of the system 100. For example, the report 260 may be displayed on the display 106 and/or user interface 104 (FIG. 1). The report 260 relates to a single patient. In some embodiments, the report 260 includes a summary table as shown in FIG. 5 that is displayed to the user. In other embodiments, the report may be a dataset that is saved or stored in the system 100. The report 260 may be retrieved by pressing an icon along the panel 236. The report 260 may include various measurements, statistics, calculations, and findings obtained by the system 100 relating to one or more SOIs. In FIG. 5, the report 260 only shows information relating to two SOIs obtained from a single imaging session. For example, the two SOIs may have been identified in the same medical image or in different medical images (i.e., different slices) of the same dataset.

For each of the SOIs, the report 260 may include local information 262A and 262B (e.g., information on size or function of the SOI). As shown, the local information 262 includes size measurements, such as a maximum diameter, a volume, and a short axis of the corresponding SOI. However, additional measurements may be shown in the report 260. If the user would like to save the medical image that shows the corresponding SOI, the user may select a save button 264 that instructs the system 100 to save the corresponding medical image with the report 260.

Figure 6:
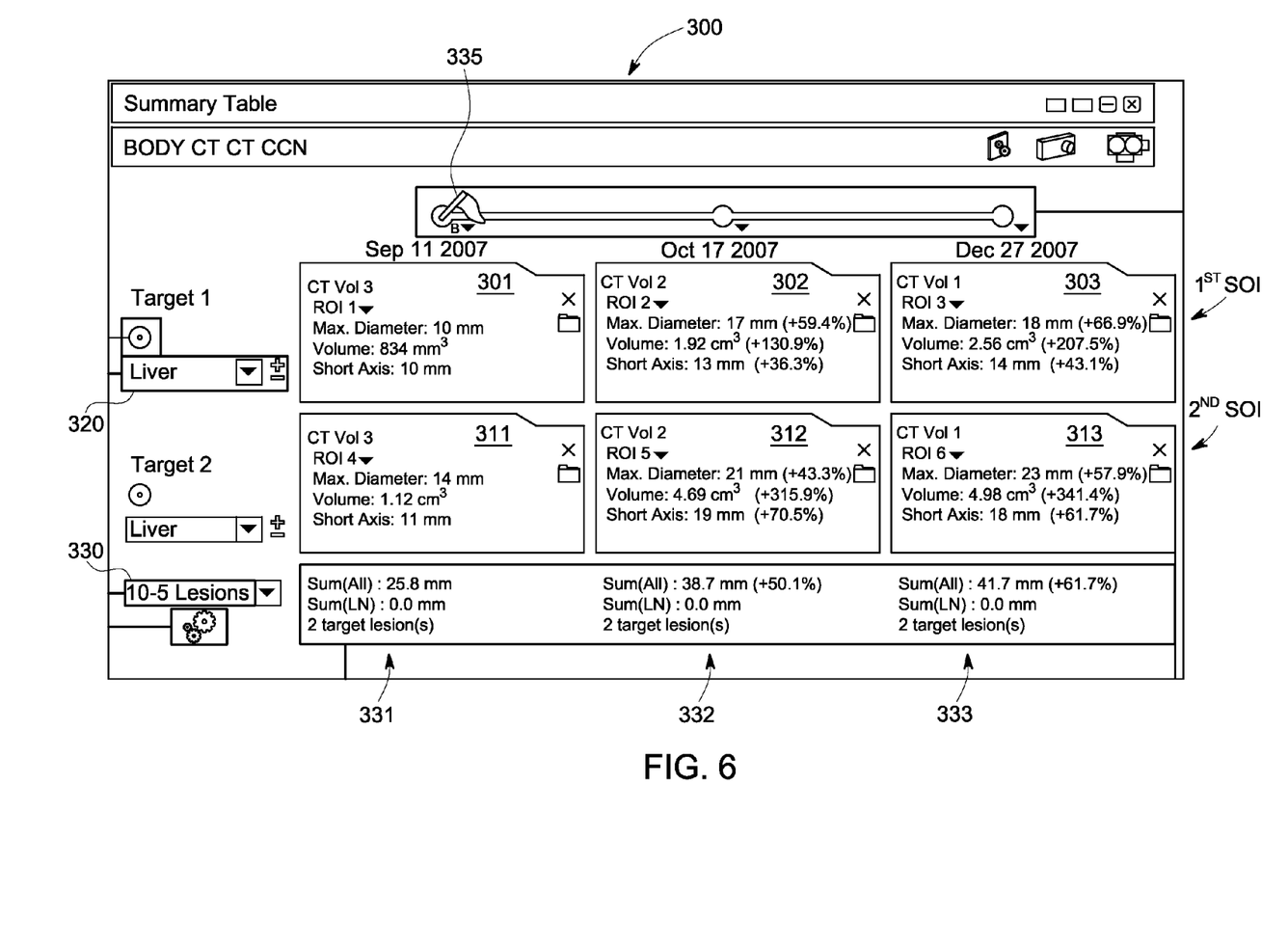
FIG. 6 illustrates another report that may be displayed to the user of the system of FIG. 1.

FIG. 6 illustrates a report 300 that may be displayed to the user of the system 100. The report 300 may be different than or a modified version of the report 260. As shown, the report 300 includes information regarding $1^{st}$ and $2^{nd}$ SOIs. The information is derived from medical images obtained at three separate times. The report 300 includes separate cells for each of the $1^{st}$ and $2^{nd}$ SOIs. Each separate cell includes information regarding the corresponding SOI that was derived from a medical image. More specifically, the cells 301-303 include local measurements of the $1^{st}$ SOI that were measured from medical images acquired at different times. The cells 311-313 include local measurements of the $2^{nd}$ SOI that were measured from medical images acquired at different times. The cells 301-303 and 311-313 are arranged to facilitate reviewing and comparing the data. For example, the cells 301-303 are arranged side-by-side along a common row, and the cells 311-313 are arranged side-by-side along a common row. In other embodiments, the cells 301-303 and the cells 311-313 may be arranged side-by-side in respective columns.

As described above, in some embodiments, when a user selects an SOI in a second medical image and obtains a second local measurement, the system 100 may automatically link the second local measurement to previous local measurement(s) of the SOI and show all local measurements associated with the SOI. As such, a user may quickly determine if the SOI has changed in size or function since the previous imaging session.

The report 300 may be characterized as a dynamic report or device that allows the user to select various options or criteria that change what is reported. For example, when second local measurements of an SOI are obtained and linked to the report 300, the system 100 may provide calculations that compare the second local measurements to one or more of the other local measurements. As shown, the size measurements in cells 302 and 303 have been compared to the size measurements in cell 301. More specifically, the $1^{st}$ SOI had a maximum diameter on Oct. 17, 2007 (e.g., a timepoint $T_2$) that was 59.4% greater than the baseline maximum diameter obtained on Sep. 17, 2007 (e.g., a timepoint $T_1$). Likewise, the $1^{st}$ SOI had a maximum diameter on Dec. 27, 2007 (e.g., a timepoint $T_3$) that was 66.9% greater than the baseline maximum diameter. The other size measurements in cells 302 and 303 show similar increases in size.

Also shown in FIG. 6, the report 300 may permit the user to select the information that will serve as a basis or reference for the other information. For example, the flag 335 indicates that the user selected the imaging session performed on Sep. 11, 2007 as the baseline imaging session. As such, data from the other imaging sessions is compared to the data of the baseline imaging session.

In addition to the above dynamic features, the report 300 may include a menu 320 that permits a user to select the anatomy in which the SOIs were found. For example, as shown in FIG. 6, the $1^{st}$ and $2^{nd}$ SOIs were found within the liver of the patient. As such, the user may manually select or set the anatomy for each identified SOI. Furthermore, the report 300 may include a menu 330 that permits the user to select the morphological criteria or standard to be used with the SOIs. For example, the user may be able to select the standard established by RECIST 1.0, RECIST 1.1, or WHO for analyzing the local measurements. The "1D-5 Lesions" as shown in FIG. 6 is used with RECIST 1.1.

Also shown in FIG. 6, the report 300 may generate outputs 331-333 after the morphological criteria are selected. For example, the report 300 may count the number of lesions that were identified from each image dataset and calculate a sum of all the maximum diameters from each image dataset. As shown in FIG. 6, the imaging session that occurred on Sep. 11, 2007 revealed 2 target lesions that had a sum of 25.8 mm. The outputs 331-333 may be determined by established standard systems, such as RECIST 1.0 or 1.1.

Figure 7:
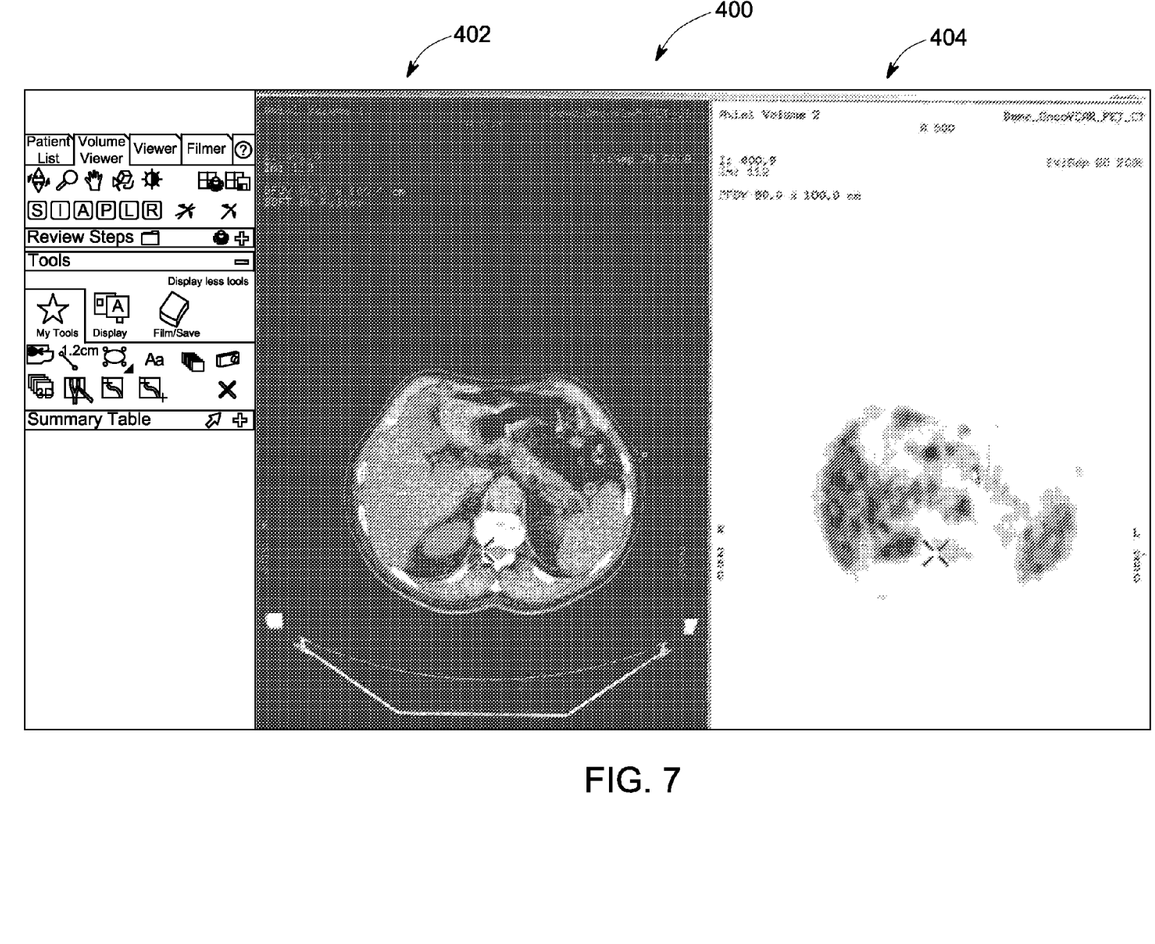
FIG. 7 illustrates a user display in accordance with one embodiment that shows different medical images acquired at different imaging sessions.

FIG. 7 illustrates a user display 400 in accordance with one embodiment that shows different medical images 402 and 404 acquired at different imaging sessions. More specifically, the medical images 402 and 404 were acquired by different imaging modalities. In the illustrated embodiment, the medical image 402 may be a CT image and the medical image 404 may be a PET image. The medical images 402 and 404 may be registered as described above with respect to the method 200. Furthermore, the SOIs identified in the medical images 402 and 404 may have local measurements subsequently determined therefrom and may be automatically linked to each other as described above with respect to he method 200. For example, each of the medical images 402 and 404 may be converted to a common coordinate system so that SOIs and local measurements may be linked.

Figure 8:
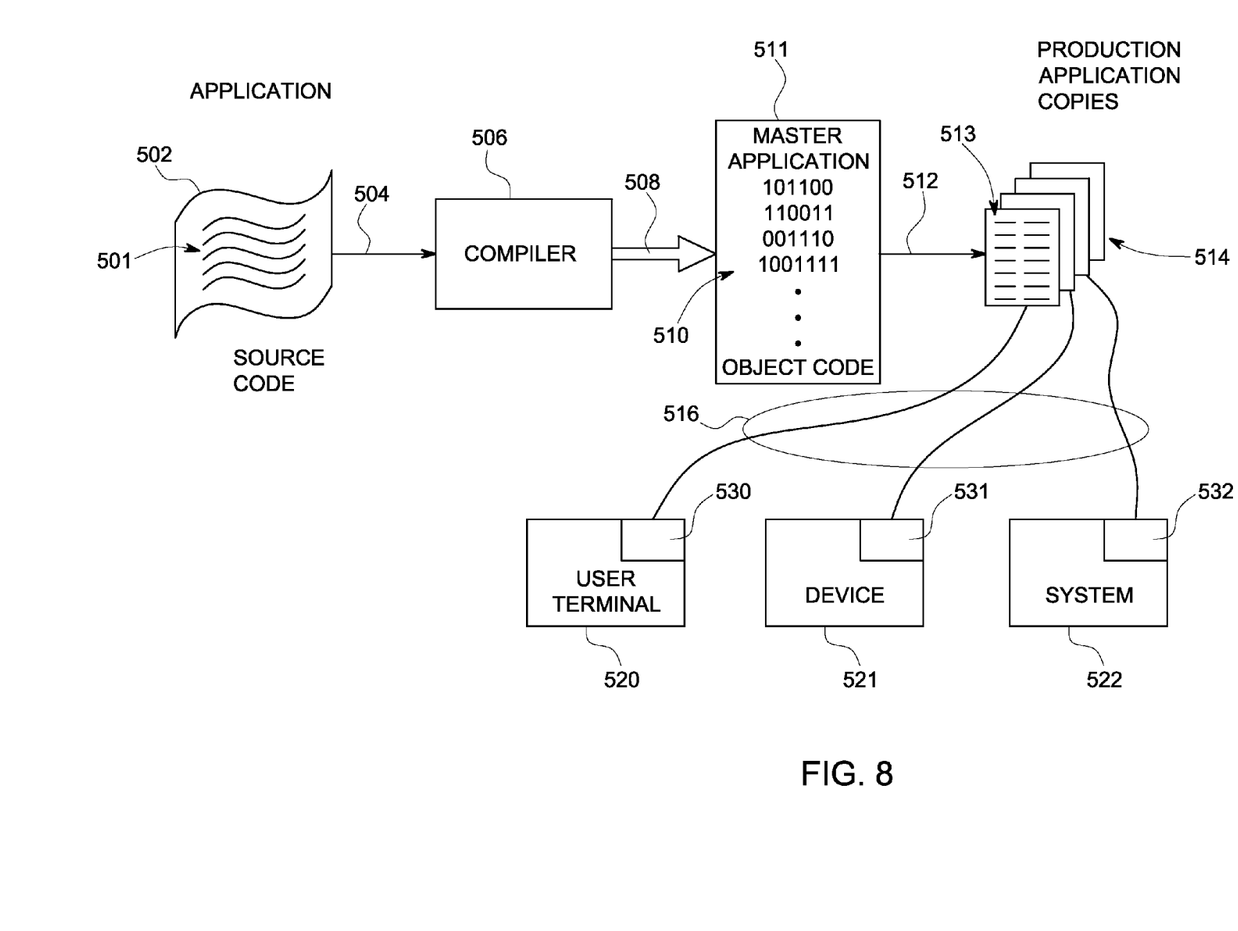
FIG. 8 is a block diagram of exemplary manners in which embodiments may be stored, distributed, and installed on computer readable medium.

FIG. 8 is a block diagram of exemplary manners in which various embodiments described herein may be stored, distributed, and installed on computer readable medium. In FIG. 8, an "application" represents one or more of the methods and process operations discussed above. As shown in FIG. 8, the application is initially generated and stored as source code 501 on a source computer readable medium 502. The source code 501 is then conveyed over path 504 and processed by a compiler 506 to produce object code 510. The object code 510 is conveyed over path 508 and saved as one or more application masters on a master computer readable medium 511. The object code 510 is then copied numerous times, as denoted by path 512, to produce production application copies 513 that are saved on separate production computer readable medium 514. The production computer readable medium 514 is then conveyed, as denoted by path 516, to various systems, devices, terminals and the like. In the example of FIG. 9, a user terminal 520, a system 521 and a system 522 are shown as examples of hardware components, on which the production computer readable medium 514 are installed as applications (as denoted by 530-532).

The source code may be written as scripts, compiled, or in any high-level or low-level language. Examples of the source, master, and production computer readable medium 502, 511, and 514 include, but are not limited to, CDROM, RAM, ROM, Flash memory, RAID drives, memory on a computing system and the like. Examples of the paths 504, 508, 512, and 516 include, but are not limited to, network paths, the internet, Bluetooth, GSM, infrared wireless LANs, HIPERLAN, 3G, satellite, and the like. The paths 504, 508, 512, and 516 may also represent public or private carrier services that transport one or more physical copies of the source, master, or production computer readable medium 502, 511, or 514 between two geographic locations. The paths 504, 508, 512, and 516 may represent threads carried out by one or more processors in parallel. For example, one computer may hold the source code 501, compiler 506 and object code 510. Multiple computers may operate in parallel to produce the production application copies 513. The paths 504, 508, 512, and 516 may be intra-state, inter-state, intra-country, inter-country, intra-continental, inter-continental and the like.

The phrases "computer readable medium" and "instructions configured to" shall refer to any one or all of i) the source computer readable medium 502 and source code 501, ii) the master computer readable medium and object code 510, iii) the production computer readable medium 514 and production application copies 513 and/or iv) the applications 530-532 saved in memory in the terminal 520, system 521 and system 522.

As used herein, the terms "computer" or "computing system" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "computing system."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes described herein. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine. The program is complied to run on both 32-bit and 64-bit operating systems. A 32-bit operating system like Windows XP™ can only use up to 3 GB bytes of memory, while a 64-bit operating system like Window's Vista™ or 7™ can use as many as 16 exabytes (16 billion GB).

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

At least one technical effect of the various embodiments of the systems and methods described herein include user-friendly interfaces and/or systems for analyzing medical images to determine whether an SOI has changed in size or function. Another technical effect includes an interface that provides quantitative and visual information regarding the SOI. Furthermore, another technical effect includes an interface that allows a user to select an SOI and automatically link local measurements of the SOI to a report or table having measurements of the SOI during different imaging sessions. In some embodiments, other technical effects include diagnosing an SOI (e.g., lesion or tumor) in a patient, managing a workflow in analyzing medical images, comparing medical images from different imaging sessions, and determining tumor response to treatment.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of analyzing a structure-of-interest (SOI) in a patient, the method comprising:

obtaining a first medical image of a patient, the first medical image including an identified structure-of-interest (SOI), the identified SOI having a corresponding local measurement;

receiving a second medical image of the patient, wherein the first and second medical images were acquired at different times;

selecting an SOI in the second medical image, the selected SOI having a corresponding local measurement;

automatically determining that the selected SOI is the identified SOI based on corresponding location data of the identified and selected SOIs, respectively, and linking the local measurements of the selected and identified SOI;

generating a report that compares the first and second local measurements, the report being displayed to the user to facilitate determining whether the identified SOI has changed in size or function;

receiving a third medical image of the patient;

selecting and SOI from the third medical image, the other selected SOI having a corresponding local measurement;

automatically determining that the identified and selected SOIs in the first, second and third medical images are a common SOI; and adding the third local measurement to the report, the report including a mathematical relationship between the first local measurement and the second local measurement and a mathematical relationship between the first local measurement and the third local measurement.

2. The method in accordance with claim 1, wherein said determining operation includes determining that a separation distance that separates the identified and selected SOIs is less than a predetermined value.

3. The method in accordance with claim 2, wherein the corresponding locations of the first and second medical images are based on centers of the identified and selected SOIs in the first and second medical images, respectively, the distance that separates the identified and selected SOIs being represented by a distance that separates the centers of the identified and selected SOIs.

4. The method in accordance with claim 1, wherein said selecting operation includes receiving user inputs that select the second SOI.

5. The method in accordance with claim 1, wherein each of the first and second local measurements are size measurements of a common type.

6. A method for generating a report including local measurements of a structure-of-interest, the method comprising:

obtaining information relating to a first medical image of a patient that includes a structure-of-interest (SOI), the information including a first local measurement of the SOI and first location data of the SOI, the first location data being indicative of where the SOI is located in the first medical image;

receiving a second medical image of the patient that includes the SOI;

determining a second local measurement of the SOI and second location data of the SOI in the second medical image, the second location data being indicative of where the SOI is located in the second medical image;

automatically linking the second local measurement of the SOI with the first local measurement of the SOI based on the first location data and the second location data, wherein said linking comprises:

calculating a center of the SOI in the first medical image based on the first location data calculating a center of the SOI in the second medical image based on the second location data, calculating a separation distance between the centers in the first and second medical images, and determining that the SOI in the first medical image and the SOI in the second medical image are separated by less than a threshold distance, wherein the threshold distance is the predetermined value; and generating a report that includes the first and second local measurements.

7. The method in accordance with claim 6 further comprising displaying the report in a user interface.

8. The method in accordance with claim 6 wherein said linking operation is performed by a linking module of a processor.

9. The method in accordance with claim 6 further comprising receiving user inputs to select the SOI in the second medical image before said determining and linking operations.

10. The method in accordance with claim 6 further comprising registering the second and first medical images.

11. An image analysis system comprising:

a database configured to store medical images, the database storing a first medical image of a patient, the first medical image including a structure-of-interest (SOI), the SOI having a first local measurement and first location data, the first location data being indicative of where the SOI is located in the first medical image;

a user interface configured to accept user inputs to select the SOI in a second medical image;

a processor configured to:

determine a second local measurement and second location data of the SOI in the second medical image, the second location data being indicative of where the SOI is located in the second medical image;

calculate a center of the SOI in the first medical image based on the first location data;

calculate a center of the SOI in the second medical image based on the second location data;

calculate a separation distance between the centers in the first and second medical images; and determine that the SOI in the first medical image and the SOI in the second medical image are separated by less than a threshold distance, wherein the threshold distance is the predetermined value; and generate a report that includes the first and second local measurements.

12. The system in accordance with claim 11 wherein the user interface is configured to display the report, the report arranging the second and first local measurements in a side-by-side manner.

13. The system in accordance with claim 11 wherein the report includes the first and second local measurements and the second and first medical images having the SOI.

14. The system in accordance with claim 11 wherein the first medical image includes at least two medical images acquired at a time point before the second medical image.

* * * * *